United States Patent
Braun et al.

(10) Patent No.: US 9,539,206 B2
(45) Date of Patent: Jan. 10, 2017

(54) METHOD FOR PRODUCING AND MONITORING ORAL ACTIVE INGREDIENT FILMS

(75) Inventors: Sebastian Braun, Wermelskirchen (DE); Armin Breitenbach, Leverkusen (DE); Ralf Schliephacke, Itzehoe (DE)

(73) Assignees: TESA SE, Norderstedt (DE); TESA LABTEC GMBH, Langenfeld (DE)

( * ) Notice: Subject to any disclaimer, the term of this patent is extended or adjusted under 35 U.S.C. 154(b) by 306 days.

(21) Appl. No.: 14/238,619

(22) PCT Filed: Jul. 9, 2012

(86) PCT No.: PCT/EP2012/063405
§ 371 (c)(1),
(2), (4) Date: Jun. 4, 2014

(87) PCT Pub. No.: WO2013/023841
PCT Pub. Date: Feb. 21, 2013

(65) Prior Publication Data
US 2014/0272099 A1    Sep. 18, 2014

(30) Foreign Application Priority Data

Aug. 12, 2011  (DE) .................. 10 2011 080 870
Dec. 16, 2011  (DE) .................. 10 2011 088 909

(51) Int. Cl.
*A61K 9/00*   (2006.01)
*A61K 9/20*   (2006.01)
(Continued)

(52) U.S. Cl.
CPC ............ *A61K 9/0056* (2013.01); *A61K 9/006* (2013.01); *A61K 9/2095* (2013.01); *A61K 9/7007* (2013.01); *A61K 47/38* (2013.01)

(58) Field of Classification Search
CPC ............ B61F 17/00; A61K 9/14; G01B 11/14
(Continued)

(56) References Cited

U.S. PATENT DOCUMENTS 4,849,246 A   7/1989   Schmidt et al.
4,915,950 A   4/1990   Miranda et al.
(Continued)

FOREIGN PATENT DOCUMENTS

DE   4230589 C1   2/1994
EP   0219762 A1   4/1987
(Continued)

OTHER PUBLICATIONS

Hoffmann E.M, et al., "Advances in orodispersible films for drug delivery", Heinrich Heine University, 2011, Germany.
(Continued)

*Primary Examiner* — Dah-Wei D Yuan
*Assistant Examiner* — Andrew Bowman
(74) *Attorney, Agent, or Firm* — Norris McLaughlin & Marcus PA

(57) ABSTRACT

Method for producing and monitoring oral active ingredient films with a base to which a solution containing at least one active ingredient is applied, the method comprising the steps: • metering and mixing the base formulation, • coating the base formulation onto a substrate, so that a strip results • if necessary, drying the base formulation strip coated on the substrate • printing a colorant solution containing at least one active ingredient onto the upper side of the base formulation strip according to the flexographic printing method, • drying the base formulation strip coated on the substrate together with the printed active ingredient solution, • penetrating the base formulation strip coated on the substrate together with the printed active ingredient solution from the upper and/or lower side by means of radiation from
(Continued)

a radiation source, • measuring the transmission of the penetrating radiation by means of at least one reception unit on the opposite side of the base formulation strip coated on the substrate together with the printed active ingredient solution.

9 Claims, 1 Drawing Sheet

(51) Int. Cl.
*A61K 9/70* (2006.01)
*A61K 47/38* (2006.01)

(58) Field of Classification Search
USPC .............. 101/36; 424/489; 427/2.1; 356/614
See application file for complete search history.

(56) References Cited

U.S. PATENT DOCUMENTS

2005/0122531 A1* 6/2005 Koele ............... A61F 13/15772
356/614

2005/0233000 A1 10/2005 Figueroa et al.
2006/0222702 A1 10/2006 Barreto et al.

FOREIGN PATENT DOCUMENTS

EP 1306071 A2 5/2003
WO 2008065144 A2 6/2008

OTHER PUBLICATIONS

Tumuluri V.S., et al., "Off-line and on-line measurements of drug-loaded hot-melt extruded films using raman spectroscopy", pp. 77-84, Department of Pharmaceutics, The University of Mississippi, 2008.
International Search Report for PCT/EP2012/063405 dated Oct. 24, 2012.
German Search Report for DE 10 2011 088 909.4 dated Jun. 21, 2012.

* cited by examiner

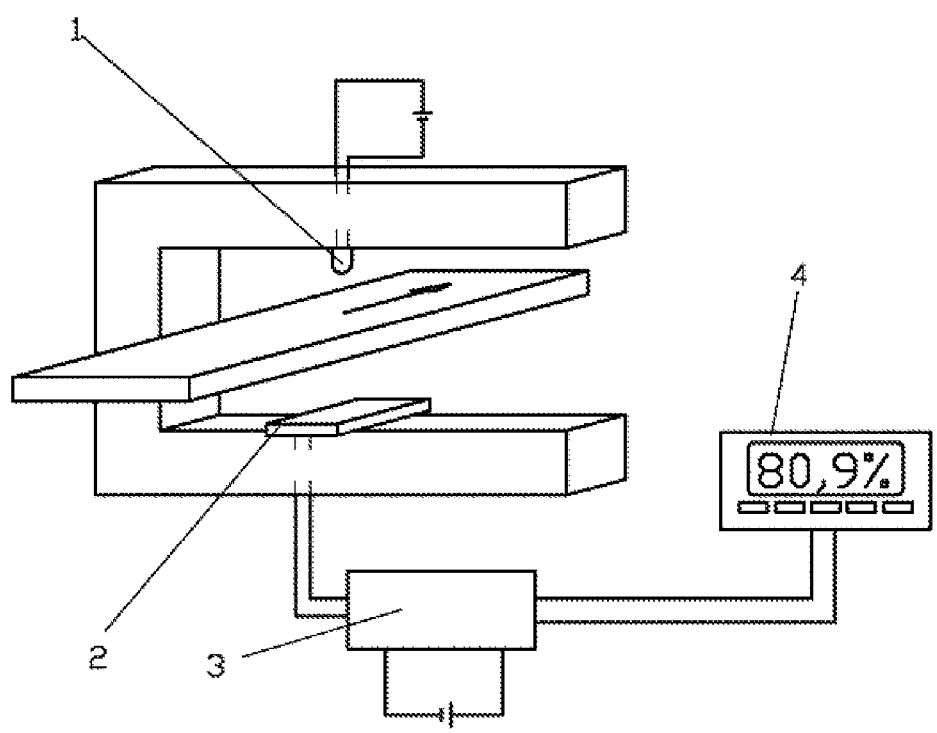

METHOD FOR PRODUCING AND MONITORING ORAL ACTIVE INGREDIENT FILMS

This application is a 35 USC 371 application of PCT/EP2012/063405 filed Jul. 9, 2012, which claims priority to the DE application 10 2011 080 870.1 filed Aug. 12, 2011 and DE application 10 2011 088 909.4 filed Dec. 16, 2011.

The invention relates to a method for producing and monitoring oral dissolvable films.

Oral dissolvable films (ODFs) are a comparatively new technology for oral delivery of active compounds. These films are extremely thin single- or multi-layer polymeric films which utilize the mouth not only for administration but also for active-compound absorption.

The film is produced using hydrophilic polymers such as cellulose or maltodextrin. The active compound can be present in the matrix of the polymers in the form of a solution, emulsion or dispersion therein. The active compound can also be in a complex-bound state. The active compound can further be present in a further layer, on the matrix. What is important is that the polymers shall dissolve rapidly on the tongue or in the oral cavity and release the active compound on its coming into contact with a liquid.

Medicinal products are primarily absorbed in the oral cavity via the buccal and sublingual mucosa. The oral mucosa is very highly perfused with blood because of a dense network of capillaries. An active compound diffusing into this microcirculatory network passes directly into the bloodstream.

These films or film strips have a limited areal extent, typically a size between 1 cm$^2$ and 10 cm$^2$ and a film thickness of 20 to 500 μm.

ODFs have come to be comparatively widely used in the form of oral hygiene strips.

Conventional methods of making ODFs of this type comprise the steps of
1. dosing and mixing the base formulation of cellulose or maltodextrin including the active compound,
2. coating the mass onto an auxiliary backing foil,
3. drying the mass coated on the auxiliary backing foil,
4. cutting and winding mother reels,
5. detaching, individualizing and sealing ODFs into a sealed pouch.

The active compound, which is very valuable, is usually dosed and added in the first step, so there will be active compound associated with the incoming and waste materials in all subsequent steps. Unnecessary losses of the valuable active compound and very costly and inconvenient cleaning and also disposal operations after production are the consequence. Costly and inconvenient monitoring is further required for the intermediate products in order that the homogeneous equidistribution of the active compound in every step may be policed.

The pharmaceutical products industry is known to employ printing processes to apply active compounds, predominantly for marking and identifying pills, tablets or capsules. This can be gleaned from US 2009/026286 A1 or WO 2006/047695 A1. Break zones on capsules or tablets are further identified by means of an intermittent, i.e., noncontinuous, method of printing, as shown by US 2007/0014852 A1 or WO 2006/058247. Ink-jet methods or tampon printing methods are customarily employed. The printing inks used therein usually contain waxes and/or fats or ingredients to enhance the mar resistance on the surfaces. WO 2005/053599 A1 describes this.

None of these cited uses require high precision in respect of the printing ink quantity, or high uniformity in the printing ink transfer to the substrate, although that would actually also not be technically possible with an intermittent process.

DE 34 23 328 A1 discloses the gravure printing process and the screen printing process as continuous printing processes for transferring adhesives which may contain active compounds.

A further problem in the manufacture of ODFs is that the mandatorily required monitoring of the active compound content usually takes the form of destructive testing of the product; that is, the individual ODF is analyzed for its constituents and the active compound content found is compared with the mandated active compound content. If there is found to be a discrepancy, this can lead to the loss of an entire batch. Economical handling of active compounds therefore requires that the monitoring take place during the continuous process of production and that the monitoring method provide a result with as short as a delay as possible, ideally immediately, in order that discrepancies in the active compound content may be responded to immediately by stopping the process. This ensures that the losses of active compounds are altogether distinctly reduced.

A typical composition of an oral dissolvable film looks as follows:
from 1 to 30 wt % of an active pharmaceutical ingredient as active compound,
from 40 to 50 wt % of a water-soluble filming polymer such as Pharmocoat or Methocel (hydroxypropylmethylcellulose),
from 0 to 20 wt % of a plasticizer such as glycerol,
from 0 to 40 wt % of fillers, dyes, aroma chemicals and further added substances.

Reference may otherwise be made to the paper "Advances in orodispersible films for drug delivery" by Hoffmann, Breitenbach and Breitkreuz in the journal *Expert Opinion on Drug Delivery*—Mar. 18, 2011, which inter alia also describes the typical ingredients of base films on page 303 and otherwise presents a very good overview of the production and properties of various oral dissolvable films.

It is an object of the present invention to provide a method for producing and monitoring oral dissolvable films which by virtue of a precise method of production and by virtue of an effective method of monitoring leads to very low losses of active compounds and which ideally prevents fluctuations in the active compound content of the oral dissolvable films.

This object is achieved by a method as set forth in the main claim. Dependent claims relate to advantageous embodiments of the method.

The present invention accordingly provides a method for producing and monitoring oral dissolvable films comprising a base whereto a solution comprising at least one active compound is applied, said method comprising the steps of
dosing and mixing the base formulation,
coating the base formulation onto a support to form a web,
optionally drying the support-coated base formulation web,
printing a dye solution comprising at least one active compound onto the upper side of the base formulation web by the flexographic printing process,
drying the support-coated base formulation web along with the printed active compound solution,
passing radiation from a radiation source from the upper and/or lower side through the support-coated base formulation web along with the printed active compound solution, measuring the transmission of the transmitted radiation on the opposite side of the support-coated base formulation web along with the printed active compound solution.

Surprisingly, the flexographic printing process as actually used in the packaging industry was found to be the best way to transfer active pharmaceutical ingredients to the base formulation web.

The flexographic printing process is a continuous printing process, offers the required high precision and secures high uniformity in the transfer of active pharmaceutical ingredients to the base formulation web. The sheer simplicity in the construction of a flexographic printing unit ensures a consistent coating process with minimal losses of printing ink quantities. The add-on can be determined by varying the configuration of the high-precision gravure roll and thus also ensures consistent uniformity of add-on. German standard specification DIN 16514: 1982-11 defines flexographic printing as a method of direct letterpress printing.

The printing form is of rubber or resilient photopolymeric plastic. The printing form is inked using an etched or engraved gravure roll of steel with chroming or ceramic (chromium oxide), the wells of which are filled with printing ink directly using a box squeegee or a dip roll. Excess ink is squeegeed off the gravure roll or (in older machines) squeezed off using a rubber roll. Printing speed varies according to the type of printing stock and motif, being 100 to 300 m/min in packaging printing. Packaging printing is the main field of deployment.

Two or more flexographic printing units can also be arranged in series in order that the add-on may be correspondingly increased.

It is advantageous in this case for the transmission to be measured after every printing operation.

In an alternative version, the printed base formulation web (post measurement) is wound up and resupplied to a flexographic printing unit. This operation can be repeated two or more times in succession until the desired amount of active compound/ingredient has been applied.

The print need not necessarily be applied uniformly in that a partial transfer of the dye solution comprising at least one active compound is likewise possible.

The proportion of active compound(s) in the dye solution comprising at least one active compound is typically between 0.01 and 25 wt %, in particular 5 to 15 wt %. The 25 wt % value, however, can also be exceeded if required in the event that this is necessary to achieve the desired effect.

The proportion of dye(s) in the dye solution comprising at least one active compound is 0.01 and 10 wt %, in particular 1 to 5 wt %. The 10 wt % value, however, can also be exceeded if required where this is necessary to achieve the desired effect.

The only dyes used should be dyes approved for use in medicinal products. Dyes of this type are found, for example, in lists issued by the Food and Drug Administration (FDA) under the heading "Summary of Color Additives for Use in United States in Foods, Drugs, Cosmetics, and Medical Devices". Specific mentions amongst these dyes may be given to Brilliant Blue FCF or E 133
(dihydrogen(ethyl)[4-[4-[ethyl(3-sulfonatobenzyl)amino]-2'-sulfonatobenzhydryl-idene]cyclohexa-2,5-dien-1-ylidene](3-sulfonatobenzyl)ammonium, disodium salt)
indigo carmine or E 132
(indigotine-5,5'-disulfonic acid, disodium salt)

The step of drying the support-coated base formulation web along with the printed active compound solution is preferably effected in a continuous manner. Suitable continuous methods of drying include hot air drying, infrared drying, high frequency drying and/or combinations thereof. The drying profile (temperature and time) involved is adjusted so as to achieve a very low residual solvent content. Suitable temperatures are between 40° C. and 150° C., while suitable drying times are in the range from 1 to 30 minutes.

The active compound content is determined according to the present invention using a dye admixture to the active compound-containing printing ink solution and a physical method of transmission measurement.

Transmission or to be more precise transmittance, or transparency, is generally reported in % and is the ratio of the luminous power arriving on the reverse side of a body irradiated with light to the luminous power incident on the front side. Transmission is curtailed by reflection and absorption.

The following equation accordingly applies: transmittance=(1−reflectance−absorptance).

The notion of transmission is widened according to the present invention to the effect that irrespective of the type of radiation used, loss of radiation on passing through the base formulation layer along with the dye and active compound add-on is defined as transmission.

The source of radiation irradiates the base formulation web along with the printed colored active compound solution. There are irradiance losses which can be detected via an appropriate detector on the opposite side of the web.

For this it is first necessary to carry out a blank measurement; that is, the base formulation web printed with the desired concentration of dye and active compound (as a precaution the actual active compound content should be confirmed with a second, different method of measurement) is irradiated and the transmission value is determined. In the rest of the procedure, then, the transmission value which is currently measured is compared with the blank value. In the event of differences between the actual measured value and the desired mandate it is possible to respond immediately, for example by stopping the process in order that the error may be eliminated. This is an effective way to reduce the losses.

Specifically when the transmission value changes continuously, for example increases monotonously, which suggests a decline in the dye and active compound content, but the value is still within the tolerance limits a loss of active compounds can even be completely avoided through an appropriate response, i.e., the immediate adjustment of the dye and active compound content.

For example, the active compound-containing printing ink solution can contain a dye which absorbs the light emitted by a red source of light. On printing a minimal quantity of dye, i.e., and also of active compound, the absorption of the light is minimal and a large amount of light is captured by a photocell as if a high dye and thus active compound quantity had been printed. The transmittance is directly dependent on the dye quantity (and hence the associated active compound quantity) and hence a direct no-contact test method for determining the active compound content without the test specimen having to be destroyed.

This also constitutes a preferred embodiment of the method, i.e., in that the radiation used is visible light and the receiving unit used is a photocell.

The monitoring method is preferably an optical method.

In a first version of the method, the step of coating the base formulation onto a support and the optional step of subsequent drying are followed by the step of diecutting the individual portions of the oral dissolvable films out of the resultant web, ideally without loss, either directly before the printing step or directly after the printing step.

In a second version of the method, the step of measuring the transmission of the transmitted radiation is followed by the step of diecutting the individual portions of the oral dissolvable films out of the base formulation web, ideally without loss.

Advantageously, the diecutting apparatus consists of a rotative cutting roll and a co-rotative opposing roll, the base formulation web being led into the nip between the cutting roll and the opposing roll. Advantageously, the base formulation web is situated on a release foil which is led over the opposing roll. In the nip, the individual contours of the diecuts are then preferably cut without web scrap, ideally without injuring the release foil (this method is known as kiss-cutting and involves cutting through the material and down to (but not right through) the foil, the release foil only being incipiently cut or minimally injured, if at all).

The diecutting apparatus further preferably consists of an up-and-down or flatbed diecutter into which the base formulation web is conveyed. A pendulum feeder upstream of the up-and-down diecutter and/or a buffer downstream of the up-and-down diecutter may be provided in order that continuous progression may be ensured for the process despite the intermittent and hence actually discontinuous operation of the up-and-down diecutter.

Finally, the individual portions of the oral dissolvable films are advantageously sealed air- and watertight in a pouch.

In one preferred embodiment of the invention, the radiation used is infrared radiation, visible light, ultraviolet radiation and/or radioactive radiation. However, the invention is not limited to the recited sources of radiation in that others are also suitable therefor.

Two or more receivers of radiation may be used—depending on the width of the web—as well as one receiver of radiation. In one version of the method, the receiver of radiation travels to and fro, in particular in the transverse direction of the base formulation web.

In a preferred version, the base formulation web is coated onto a carrier foil as support, preferably of polyethylene, said carrier foil travelling through the process together with the base formulation web. Particular preference for use as support is given to a foil of polyester, most preferably of polyethylene terephthalate (PET).

The thickness of the release foil is in particular between 60 and 150 μm.

The thickness of the base formulation web is usually between 25 to 200 μm, in particular between 65 to 100 μm.

The width of the base formulation web is preferably between 20 and 35 mm and is very advantageously 30 mm.

The method is preferably carried out continuously in one operation.

However, it is also possible for the step of coating the base formulation onto the support, preferably a release foil, and the optional step of then drying the base formulation web to be followed by interrupting the method to the effect that the base formulation web is initially wound up to form reels, for example with lengths of 300 m to 500 m.

These reels can then be stored or shipped to a further processor. The reels are unwound as required, and the method of the present invention starts with the step of printing a dye solution comprising at least one active compound onto the upper side of the base formulation web by the flexographic printing process.

Typical active compounds are—without completeness being claimed in the context of the present invention:

antiallergics, antiarrhythmics, antibiotics, antidiabetics, antiepileptics, antihistamines, anti-tussives, cardiotonics, diuretics, hypotensives, narcotics, neuromuscular blockers, sexual hormones and also vasopressors. These can also be used in mixtures, depending on the therapeutically desired result.

Useful active compounds for the purposes of the present invention further include menthol, a substance familiar from oral hygiene strips, in addition to other flavor, aroma or scent chemicals of the kind used in the oral hygiene sector.

Typical polymers for forming the base formulation film are cellulose derivatives such as hydroxypropylmethylcellulose, hydroxyethylcellulose and/or hydroxypropylcellulose and also maltodextrin. These polymers can be used singly or in any desired mixtures.

Useful sources of radiation include light sources that emit in the desired wavelength region. Radioactive emitters can also be used.

The receiving unit takes the form of photocells. In the case of radioactive radiation, one or more Geiger counters suffice to detect the radiation.

By combining the very precise and reliable flexographic printing process with the in-line method of measurement which delivers an instantaneous result, the invention avoids excessive losses of active compound and the resultant costly and inconvenient cleaning and disposal operations in the event of faulty production, as well as the need for monitoring intermediate products.

In summary, the method involves simple and compact machinery and permits rapid changeover to other drug-containing printing inks without cross contamination between different active compounds.

The later the valuable active compound is applied in the ongoing process, the lower the losses thereof are in the event that the concentration differs from the mandated value.

The very advantageous combination of flexographic printing with in-line measurement makes it possible to achieve processing speeds of up to 100 m/min.

An example of the invention will now be more particularly described without any intention to restrict the invention.

EXAMPLE

A flexographic printing press was fitted with a chromed gravure roll having a screen frequency of 54 lines per cm, a well depth of 40 μm and a theoretical scooping volume of 11.7 $cm^3/m^2$. The printing cylinder used was an EPDM-coated rubber roll. An opposing cylinder combines with the printing cylinder to form a roll nip in which the print takes place according to the flexographic mode of printing known to a person skilled in the art. The base formulation web, which was led into the roll nip via the opposing cylinder, was an ODF base film material reel 20 mm in width and 100 m in length, the main constituent of which is hydroxypropylmethylcellulose.

The printing ink solution, consisting of 4.4 wt % of hydroxypropylcellulose, 8.9 wt % of active pharmaceutical ingredient, 2.3 wt % of blue dye and 84.4 wt % of ethanol, is printed onto the base formulation web at a printing speed of 15 m/min.

The printing unit is followed by a dryer unit where the solvent, in the form of ethanol, evaporates via convective drying. The printed tape is subsequently wound up to form a reel and is printed three times in succession without revamping the flexographic printing unit.

The transmission measurements obtained for the base formulation web printed on its upper side with the colored solution comprising an active compound were measured using a red luminescent diode (wavelength 650 nm) as depicted in FIG. 1, and found to be:

without printing=blank value=80.9%
printed 1×: 74.7%
printed 2×: 64.7%
printed 3×: 56.7%

The amount of active pharmaceutical ingredient on the base formulation web, as determined by a chemical method of analysis, was found to be:

without printing=blank value=0.00 mg/6 cm$^2$
printed 1×: 0.34 mg/6 cm$^2$
printed 2×: 0.63 mg/6 cm$^2$
printed 3×: 0.87 ring/6 cm$^2$ As can be seen, the transmission value decreases with increasing concentration of dye and hence of active compound.

The transmission value is determined for a predetermined concentration. Deviations from this transmission value which are outside the mandated error tolerances are detected in-line and thus instantaneously, enabling very rapid intervention in the process.

LIST OF REFERENCE SIGNS 1 red LED light source
2 photocell (receiver)
3 OP amplifier
4 indication of transmission value

What is claimed is:

1. A method for producing and monitoring oral dissolvable films comprising a base whereto a solution comprising at least one active compound is applied, said method comprising the steps of
    (a) dosing and mixing a base formulation,
    (b) coating the base formulation onto a support to form a support-coated base formulation web,
    (c) optionally drying the support-coated base formulation web,
    (d) printing a dye solution comprising the at least one active compound onto an upper side of the support-coated base formulation web by flexographic printing, thereby obtaining a printed active compound solution,
    (e) drying the support-coated base formulation web along with the printed active compound solution,
    (f) passing radiation from a radiation source from the upper and/or a lower side through the support-coated base formulation web along with the printed active compound solution,
    (g) measuring transmitted radiation using at least one receiving unit on a side of the support-coated base formulation web which is opposite to the radiation source, along with the printed active compound solution, wherein the transmission of the transmitted radiation correlates with the concentration of the at least one active compound, thereby measuring the concentration of the at least one active compound.

2. The method as claimed in claim 1, wherein step (b) and optional step (c) are followed by a step (b)(1) of diecutting individual portions of the oral dissolvable films out of the optionally dried support-coated base formulation web either directly before step (d) or directly after step (d).

3. The method as claimed in claim 1, wherein step (g) is followed by a step (g)(1) of diecutting individual portions of the oral dissolvable films out of the support-coated base formulation web.

4. The method as claimed in claim 1, wherein individual portions of the oral dissolvable films produced by said method are sealed in a pouch in a final step.

5. The method as claimed in claim 1, wherein radiation used in step (f) is infrared radiation, visible light, ultraviolet radiation and/or radioactive radiation.

6. The method as claimed in claim 5, wherein radiation used in step (f) is visible light and the at least one receiving unit used is a photocell.

7. The method as claimed in claim 1, wherein the support-coated base formulation web is coated onto a release foil.

8. The method as claimed in claim 1, wherein thickness of the support-coated base formulation web is between 25 to 200 μm.

9. The method as claimed in claim 1, which is carried out continuously.

* * * * *